United States Patent
Ledoux et al.

(10) Patent No.: US 8,411,822 B2
(45) Date of Patent: *Apr. 2, 2013

(54) METHODS AND SYSTEMS FOR DETERMINING THE AVERAGE ATOMIC NUMBER AND MASS OF MATERIALS

(75) Inventors: Robert J. Ledoux, Harvard, MA (US); William Bertozzi, Lexington, MA (US)

(73) Assignee: Passport Systems, Inc., Billerica, MA (US)

(*) Notice: Subject to any disclaimer, the term of this patent is extended or adjusted under 35 U.S.C. 154(b) by 0 days.

This patent is subject to a terminal disclaimer.

(21) Appl. No.: 13/275,909

(22) Filed: Oct. 18, 2011

(65) Prior Publication Data

US 2012/0183125 A1    Jul. 19, 2012

Related U.S. Application Data

(63) Continuation of application No. 12/578,956, filed on Oct. 14, 2009, now Pat. No. 8,041,007, which is a continuation of application No. 11/854,213, filed on Sep. 12, 2007, now Pat. No. 7,634,058, which is a continuation of application No. 11/177,758, filed on Jul. 8, 2005, now Pat. No. 7,286, 638.

(60) Provisional application No. 60/586,351, filed on Jul. 8, 2004.

(51) Int. Cl.
*G01N 23/201* (2006.01)

(52) U.S. Cl. ............................................ 378/88; 378/57

(58) Field of Classification Search ................. 378/5, 19, 378/51, 53, 57, 70, 86–88
See application file for complete search history.

(56) References Cited

U.S. PATENT DOCUMENTS

| | | | | |
|---|---|---|---|---|
| 7,286,638 B2* | 10/2007 | Ledoux et al. | | 378/88 |
| 7,634,058 B2* | 12/2009 | Ledoux et al. | | 378/88 |
| 8,041,007 B2* | 10/2011 | Ledoux et al. | | 378/88 |
| 2007/0025505 A1* | 2/2007 | Bjorkholm | | 378/53 |

* cited by examiner

*Primary Examiner* — Courtney Thomas
(74) *Attorney, Agent, or Firm* — Foley Hoag LLP

(57) ABSTRACT

Disclosed herein are methods and systems of scanning a target for potential threats using the energy spectra of photons scattered from the target to determine the spatial distributions of average atomic number and/or mass in the target. An exemplary method comprises: illuminating each of a plurality of voxels of the target with a photon beam; determining an incident flux upon each voxel; measuring the energy spectrum of photons scattered from the voxel; determining, using the energy spectrum, the average atomic number in the voxel; and determining the mass in the voxel using the incident flux, the average atomic number of the material in the voxel, the energy spectrum, and a scattering kernel corresponding to the voxel. An exemplary system may use threat detection heuristics to determine whether to trigger further action based upon the average atomic number and/or mass of the voxels.

40 Claims, 5 Drawing Sheets

METHODS AND SYSTEMS FOR DETERMINING THE AVERAGE ATOMIC NUMBER AND MASS OF MATERIALS

CROSS-REFERENCE TO RELATED APPLICATION

This application is a continuation of U.S. Ser. No. 12/578.956 filed on Oct. 14, 2009, U.S. Ser. No. 11/854,213 filed on Sep. 12, 2007, and U.S. Ser. No. 11/177,758 filed on Jul. 8, 2005, which claims priority to U.S. Ser. No. 60/586,351 filed on Jul. 8, 2004 and is hereby incorporated by reference.

BACKGROUND OF THE INVENTION

1. Field of the Invention

This invention relates to the field of non-intrusive scanning, and more particularly to systems and methods of determining the average atomic number and mass of a target or one or more portions of a target, as well as to systems and methods of obtaining limits on the mass of certain elements present in a target or in one or more portions of a target.

2. Background Information

A desirable characteristic of a non-intrusive inspection technique for inspecting a target is the ability to rapidly determine atomic number (Z) and density of the target material, as well as the spatial distribution of atomic number and density. In particular, a rapid determination, preferably with low radiation dose, of the distribution in three dimensions of average atomic number and/or mass is a powerful and useful means to determine the contents of a target container. This information may be used to determine a probability that a target container such as a piece of luggage, a shipping container, a storage container, or other container for land, sea, or air transport contains a certain material, such as for example a high-Z and/or a high-density material. Knowledge that a target container contains such a material may be used to identify a threat. For example, the presence of lead in a container may indicate shielding for a "dirty bomb" or other radioactive material. The presence of high Z materials such as uranium may signal the presence of a nuclear weapon in the container. Moreover, measurement of mass distribution, average atomic number, or both may form part of a sequence of inspection techniques. For example, regions of the target that are determined to match specified Z and density categories can be used as input into other inspection techniques that will further probe these regions. Such a system may offer the advantage of providing threat determinations in a convenient time scale.

Techniques for the non-intrusive inspection of cargo include the detection of transmitted radiation (as in x-ray imaging) to obtain a two-dimensional representation of the distribution of density in a target cargo container. Two-dimensional imaging using scattered radiation, such as Compton-scattered radiation, has also been demonstrated. Because of the limitations of two-dimensional imaging, it is often desirable to obtain the density distribution in three dimensions. Non-intrusive scanning to obtain both two- and three-dimensional images of a target using nuclear resonance fluorescence techniques has been described, for example, in U.S. Pat. No. 5,115,459, Explosives Detection Using Resonance Fluorescence of Bremsstrahlung Radiation, and U.S. Pat. No. 5,420,905, Detection of Explosives and Other Materials Using Resonance Fluorescence, Resonance Absorption, and Other Electromagnetic Processes with Bremsstrahlung Radiation, the contents of both of which are hereby incorporated by reference.

SUMMARY OF THE INVENTION

Methods and systems for achieving non-intrusive inspection of cargo, shipping containers, luggage, and other targets via measurements of scattered photon energy spectra resulting from the scattering of photon beams are presented here. The methods and systems presented here take advantage of processes that contribute to the 511 keV annihilation peak and higher-order processes, some occurring at higher energies, which exhibit stronger Z-dependence than such processes as Compton or Rutherford scattering. The methods and systems disclosed also benefit from the greater penetration of radiation that occurs at energies above the K-edge for most materials, allowing fewer losses in the target of photons that would otherwise contribute to signal from deep in the target. This allows the inspection of larger and/or denser targets than may be practicable with systems operating at lower photon energy. Additionally, the methods presented here may be employed to obtain a two-dimensional and three-dimensional average atomic number and/or density as well as mass limits on the presence of high-Z material, data more rapidly and with lower radiation dose than NRF imaging.

In one aspect, a method for analyzing the material in a voxel of a target comprises illuminating the voxel with a photon beam; measuring a first number of photons scattered from the voxel in a first energy range and in a first measurement direction; measuring a second number of photons scattered from the voxel in a second energy range and in a second measurement direction; determining a ratio of the first number of photons to the second number of photons; and determining an average atomic number of the material in the voxel using the ratio. In further embodiments, the first energy range includes 511 keV. In further embodiments, the second energy range excludes 511 keV. In other embodiments, the first direction is the same as the second direction.

In another aspect, a method for analyzing the material in a voxel of a target, comprises illuminating the voxel with a photon beam; measuring an energy spectrum of photons scattered from the voxel in a measurement direction; determining a first number of photons contributing to the energy spectrum in a first energy range; determining a second number of photons contributing to the energy spectrum in a second energy range; computing a ratio of the first number of photons to the second number of photons; and determining an average atomic number of the material in the voxel using the ratio. In further embodiments, the first energy range includes 511 keV. In further embodiments, the second energy range excludes 511 keV.

In another aspect, a system for analyzing the material in a voxel of a target comprises a device for generating a photon beam; a first detector configured to detect a first energy spectrum of photons scattered from the voxel in a first measurement direction; and a processor; wherein the processor is configured to determine a ratio of a first number of scattered photons having energies in a first energy range to a second number of scattered photons having energies in a second energy range; and wherein the processor is further configured to determine the average atomic number in the voxel. In other embodiments, a system for analyzing the material in a voxel of a target further comprises a second detector configured to detect a second energy spectrum of photons scattered from the voxel in a second measurement direction. In still further embodiments, the first angle is the same as the second angle.

In still further embodiments, the first energy range includes 511 keV. In still further embodiments, the second energy range excludes 511 keV.

In another aspect, a method of analyzing material in a voxel of a target comprises illuminating the voxel with a photon beam; determining an incident flux upon the voxel; measuring at least one energy spectrum of photons scattered from the voxel; determining, using the measured energy spectrum, the average atomic number in the voxel; and determining the mass in the voxel using the incident flux, the average atomic number of the material in the voxel, the measured energy spectrum, and predetermined values of a scattering kernel corresponding to the voxel. In still further embodiments, determining the average atomic number in the voxel comprises determining a first number of photons contributing to at least one of the energy spectra in a first energy range; determining a second number of photons contributing to at least one of the energy spectra in a second energy range; computing a ratio of the first number of photons to the second number of photons; and determining an average atomic number of the material in the voxel using the ratio. In still further embodiments, the first energy range includes 511 keV. In still further embodiments, the second energy range excludes 511 keV.

In another aspect, method of analyzing material in a plurality of voxels of a target, comprises (a) illuminating the voxels with a photon beam; (b) measuring, for each of the voxels, at least one energy spectrum of photons scattered from the voxel; (c) for each of the voxels, determining the average atomic number of the material in the voxel, using the measured energy spectrum; and (d) for each voxel, (I) determining an incident flux upon the voxel; and (ii) determining the mass in the voxel using the incident flux, the average atomic number of the material in the voxel, the measured energy spectrum, and predetermined values of a scattering kernel corresponding to the voxel. In further embodiments, determining the average atomic number in each of the voxels comprises determining a first number of photons contributing to at least one of the energy spectra in a first energy range; determining a second number of photons contributing to at least one of the energy spectra in a second energy range; computing a ratio of the first number of photons to the second number of photons; and determining an average atomic number of the material in the voxel using the ratio. In further embodiments, the first energy range includes 511 keV. In still further embodiments, the second energy range excludes 511 keV.

In another aspect, a method of analyzing material in a plurality of voxels of a target comprises (a) illuminating the voxels with a photon beam; (b) measuring at least one energy spectrum of photons scattered from each of the voxels; (c) determining, using the measured energy spectrum, the average atomic number in each of the voxels; (d) for each voxel, (i) determining a flux of photons incident, on the voxel; and (ii) using the average atomic number, the measured energy spectrum, and predetermined values of a scattering kernel to determine the average mass in the voxel; (e) computing, using the estimated average mass and average atomic number in each voxel, an estimated exit flux exiting the target; measuring a measured exit flux exiting the target; computing a difference between the estimated exit flux and the measured exit flux; and computing a correction to the estimated average mass in each voxel based upon the computed difference between the estimated exit flux and the exit flux. In further embodiments, computing a correction to the estimated average mass in each voxel further comprises assigning, for each voxel, a contribution to the computed difference between the estimated exit flux and the exit flux in proportion to the estimated average mass in that voxel. In further embodiments, computing a correction to the estimated average mass in each voxel further comprises using a minimization procedure to adjust the estimated average mass in each voxel so that the computed difference between the estimated exit flux and the exit flux is minimized. In still further embodiments, computing a correction to the estimated average mass in each voxel further comprises adjusting the computed average atomic number in each voxel so that the computed difference between the estimated exit flux and the exit flux is minimized.

In another aspect, a method of analyzing material in a voxel of a target comprises (a) illuminating the voxel with a photon beam; (b) determining an incident flux incident on the voxel; (c) measuring at least one energy spectrum of photons scattered from the voxel; (d) determining the mass in the voxel by (i) determining, using the incident flux and the measured energy spectrum, the average atomic number in the voxel; and (ii) using the average atomic number, the measured energy spectrum, and predetermined values of a scattering kernel to determine the mass in the voxel; and (e) determining an upper limit on a mass of a selected species present in the voxel, using the measured energy spectrum, and the mass in the voxel. In further embodiments, determining an upper limit on a mass of selected species present in the voxel comprises evaluating a first scattering kernel corresponding to the selected species, and evaluating a second scattering kernel corresponding to a second species. In still further embodiments, determining the average atomic number in each voxel comprises determining a first number of photons contributing to at least one of the energy spectra in a first energy range; determining a second number of photons contributing to at least one of the energy spectra in a second energy range; computing a ratio of the first number of photons to the second number of photons; and determining an average atomic number of the material in the voxel using the ratio. In still further embodiments, the first energy range includes 511 keV. In still further embodiments, the second energy range excludes 511 keV.

In another aspect, a system for determining the average atomic number in a voxel of a target, the system comprises a photon beam; a means for determining an incident flux incident on the voxel; a detector configured to view the target and equipped to detect an energy spectrum of photons scattered from the voxel; and a processor; wherein the processor is configured to determine, using the energy spectrum, the average atomic number in the voxel; and the processor is further configured to determine the average atomic mass in the target voxel using the incident flux, the average atomic number, the energy spectrum, and predetermined values of a scattering kernel.

In another aspect, a method of analyzing material in a voxel of a target, comprises illuminating the voxel with a photon beam; determining an incident flux upon the voxel; measuring at least one energy spectrum of photons scattered from the voxel; determining a first number of photons contributing to at least one of the energy spectra in a first energy range, the first energy range including 511 keV; determining a second number of photons contributing to at least one of the energy spectra in a second energy range; computing a ratio of the first number of photons to the second number of photons; using a correlation between the ratio and the first number of photons to determine a probable average atomic number and mass in the voxel. In further embodiments, the second energy range excludes 5.11 keV.

The present disclosure also describes methods and systems for scanning a target for potential threats. In one aspect, a method of scanning a target for potential threats comprises:

(a) for each of a plurality of voxels in the target: (i) illuminating the voxel with a photon beam; (ii) measuring an energy spectrum of photons scattered from the voxel in a measurement direction; (iii) determining a first number of photons contributing to the energy spectrum in a first energy range; (iv) determining a second number of photons contributing to the energy spectrum in a second energy range; (v) computing a ratio of the first number of photons to the second number of photons; and (vi) determining an average atomic number of the material in the voxel using the ratio; and (b) determining whether to trigger further action using the average atomic numbers of each of the plurality of voxels. In further embodiments, the first energy range includes 511 keV. In still further embodiments the second energy range excludes 511 keV. In still further embodiments, the method further comprises displaying the spatial distribution of the average atomic numbers on an output device. In still further embodiments, further action comprises scanning a portion of the target by nuclear resonance fluorescence, or notifying an operator that suspicious material may be present.

In another aspect, a method of scanning a target for potential threats, comprises (a) for each of a plurality of voxels in the target: (i) illuminating the voxel with a photon beam; (ii) measuring a first number of photons scattered from the voxel in a first energy range and in a first measurement direction; (iii) measuring a second number of photons scattered from the voxel in a second energy range and in a second measurement direction; (iv) determining a ratio of the first number of photons to the second number of photons; and (v) determining an average atomic number of the material in the voxel using the ratio; and (b) determining whether to trigger further action using the average atomic numbers of the material in each of the plurality of voxels In further embodiments, the first energy range includes 511 keV. In still further embodiments, the second energy range excludes 511 keV. In still further embodiments, the method further comprises displaying the spatial distribution of the average atomic numbers on an output device. In still further embodiments, further action comprises scanning a portion of the target by nuclear resonance fluorescence, or notifying an operator that suspicious material may be present.

In another aspect, a method of scanning a target for potential threats, comprises (a) for each of a plurality of voxels in the target: (i) illuminating the voxel with a photon beam; (ii) determining an incident flux upon the voxel; (iii) measuring at least one energy spectrum of photons scattered from the voxel; (iv) determining, using the measured energy spectrum, the average atomic number in the voxel; and (v) determining the mass in the voxel using the incident flux, the average atomic number of the material in the voxel, the measured energy spectrum, and predetermined values of a scattering kernel corresponding to the voxel; determining whether to trigger further action using the masses and the average atomic numbers in each of the plurality of voxels.

In another aspect, a system for scanning a target for threatening material comprising: a means for generating a beam of photons; a means for translating the target relative to the beam of photons; at least one detector configured to detect at least one energy spectrum of photons scattered in a measurement direction from at least one voxel of the target; and a processor; wherein the processor is configured to determine a ratio of a first number of scattered photons having energies in a first energy range to a second number of scattered photons having energies in a second energy range; the processor is further configured to determine the average atomic number in the voxel; the processor is further configured to use the average atomic number in the voxel to determine whether to trigger further action.

BRIEF DESCRIPTION OF THE DRAWINGS

The invention description below refers to the accompanying drawings, of which.

DETAILED DESCRIPTION OF AN ILLUSTRATIVE EMBODIMENT

To provide an overall understanding, certain illustrative embodiments will now be described; however, it will be understood by one of ordinary skill in the art that the devices and methods described herein can be adapted and modified to provide devices and methods for other suitable applications and that other additions and modifications can be made without departing from the scope of the systems described herein.

Unless otherwise specified, the illustrated embodiments can be understood as providing exemplary features of varying detail of certain embodiments, and therefore, unless otherwise specified, features, components, modules, and/or aspects of the illustrations can be otherwise combined, specified, interchanged, and/or rearranged without departing from the disclosed devices or methods. Additionally, the shapes and sizes of components are also exemplary, and unless otherwise specified, can be altered without affecting the disclosed devices or methods.

Some exemplary systems for employing continuous-spectrum photon sources such as bremsstrahlung sources in resonant scattering measurements (also called nuclear resonance fluorescence or NRF) in non-intrusive scanning applications are discussed in U.S. Pat. Nos. 5,115,459, and 5,420,905. The methods and systems described herein may employ similar apparatus for measurements using non-resonant scattering processes.

Figure 1:
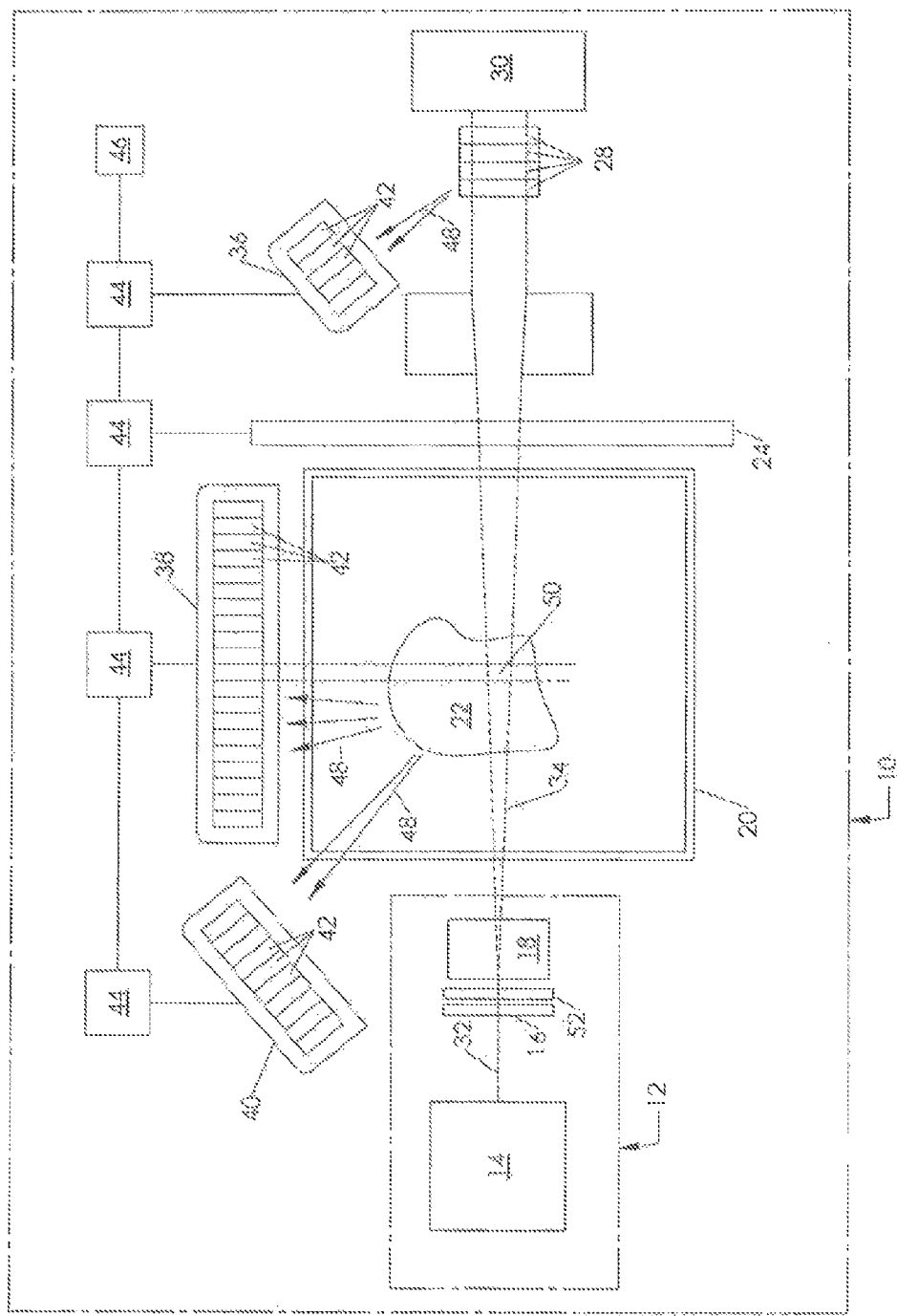
FIG. 1 is a schematic diagram of an exemplary embodiment of a scanner configuration.

A schematic diagram of an exemplary embodiment of a scanner configuration is shown in FIG. 1.

The system includes a photon source 12 producing photons having an energy spectrum over some energy range. Suitable photon sources may include: a bremsstrahlung source; a Compton-broadened photon source using nuclear decay from a radioactive source; coherent bremsstrahlung radiation; free electron lasers; laser backscatter from high energy electrons; neutron capture photons; or other photon sources known to those skilled in the field.

In the embodiment illustrated in FIG. 1, the photon source 12 may be a bremsstrahlung source and may include an electron source 14 providing a beam of electrons 32 incident on a bremsstrahlung target 16 to generate a bremsstrahlung photon beam 34. The bremsstrahlung target 16 may be followed by a beam stopper (not illustrated) to stop the electrons 32. A filter 52 may follow the beam, stopper to filter out low energy photons from the bremsstrahlung beam 34 if desired. A collimator 18 may be employed to collimate the bremsstrahlung beam 34. Shielding (not illustrated) may enclose the photon source 12. A description of an exemplary suitable bremsstrahlung photon source may be found in U.S. Pat. No. 5,115,459.

A target 20 to be scanned, such as a cargo container, shipping container, luggage, package, or other container or object, may be placed in the path, of the photon beam 34. In one embodiment, the target may be moved through the path of the beam, for example by a conveyor belt. In another embodiment, the beam 34 may be scanned across the target 20, for example, by moving photon source 12 or steering the electron beam 32. Other ways of achieving scanning of the photon beam 34 over the target container 20 will be recognized by those skilled in the art. The target 20 may contain target contents 22. The incident photon beam 34 impinges upon the target container 20, and photons 48 may be both scattered from the contents 22 and the target 20 as well as transmitted through the contents 22 and the target 20.

Detecting apparatuses 38 and 40, which may include an array of detectors 42, may capture, measure, count, and/or record the energies of the photons scattered in a given direction or directions. A description of several exemplary suitable detecting apparatuses may be found in U.S. Pat. No. 5,115,459. The detecting apparatus 38 or 40 may further include a filter over the face of each detector to absorb low energy photons, and shielding (not illustrated). As scattering from the collimating aperture 18 could lead to a significant amount of photons directed toward the detecting apparatus 38 or 40, a shadow shield (not illustrated) between the collimator and the detecting apparatus 38 or 40 may be employed. A beam dump 30 may be provided to absorb the energy of the beam 34 that is not absorbed as the beam 34 passes through the target 20. Shielding (not shown) may enclose the entire device while allowing convenient means for the entry and exit of targets.

Data from the detecting apparatus 38 or 40 is sent to a processor 46 which may analyze the data, for example, to determine an average atomic number, mass, or upper limits on a mass of a selected element as described below. The data may be preprocessed by preprocessing electronics 44, which may include preamplifiers, filters, timing electronics, and/or other appropriate preprocessing electronics. (Although the preprocessing electronics 44 are connected serially in the figure, they may also be connected in parallel to the processor 46.) The processor 46 may be further adapted to evaluate the data to determine whether the contents of the target volume meet or exceed one or more predetermined detection thresholds. For example, the processor 46 may compare the data for each irradiated target volume to profiles of "normal" target volumes to determine whether the irradiated target volume should be considered "suspicious." In addition, the processor 46 may be programmed with other threat detection heuristics as described below. Further, as described in more detail below, the processor 46 may control a variety of parameters of the photon beam, scanning, detection, and/or other aspects of the system.

The detecting apparatus 38 and/or 40 may be configured to view the target 20 at a measurement angle θ with respect to the photon beam 34 of more than 90 degrees relative to the direction of the photon beam. In an exemplary embodiment, the detecting apparatus 40 views the target at a measurement angle of approximately 130 degrees.

The beam 34 passes through the target contents 22. This beam may be absorbed in a beam dump 30 designed to absorb substantially all of the remaining energy. For example, a suitable beam dump for 10 MeV may include a layer of a hydrogenous material containing boron or lithium, a layer of carbon, and a layer of iron in a cavity formed in a shield of lead and/or iron to shield the sides and the detectors from back-streaming low energy photons. A layer of a hydrogenous material containing boron or lithium may surround the outside of this shield. The depth of this cavity, the beam dimensions, the directional collimation of the detectors, and the exact location of the detectors are related parameters that may be made compatible so as to minimize the number of backward-streaming photons from the beam dump entering the detectors. Additional shadow shields may be set up to help meet this goal.

Scanning can be achieved in a variety of ways with the technique described herein. The luggage can be scanned with the beam by moving the entire photon source 12, the target 20, or simply the aperture 18. The electron beam may also be deflected by a magnet to sweep the photon beam direction. Preferred photon beam geometries include spots (cones) and stripes. Other suitable scanning configurations, geometries, and patterns may be recognized by those skilled in the art and may be employed.

For example, in one embodiment, if the beam 34 is collimated using a small circular aperture 18 to an average angle of approximately 1/20 radians (about 3 degrees), the spot 1 meter from the aperture may be about 10 cm across, a suitable size for imaging the contents of a piece of luggage. If higher resolution is desired, a more tightly collimated beam may be used. Alternatively, larger spot sizes may be preferred for rapid scanning and/or for larger targets.

If the photon beam 34 is collimated using a vertical slit aperture to produce a thin stripe of 10 cm width at the point of incidence with a piece of luggage, for example, a 60 cm long suitcase could be scanned in a few seconds as the suitcase moves on a conveyor belt. Alternatively, the photon beam 34 could be collimated into a spot swept vertically by an adjustable collimator or by magnetic deflection of the electron beam 32 used to generate the photon beam 34. Even if the collimation is in the form of a vertical stripe, the central intensity remains the highest, reflecting the natural collimation, and magnetic deflection of the electron beam 32 may be useful for imaging. In other embodiments, stripes with configurations other than vertical may be employed.

In addition, in some embodiments, a pulsed photon beam may be used to allow spatial resolution. Where the photon source is generated by an electron accelerator with suitable pulse structure, the relative time between the photon pulse and the time of detection can be used to infer the spatial position of possible interaction points.

A target 20 may be conceptualized as divided into portions or "voxels." Each voxel is defined by the three dimensional intersection of the photon beam 34 with the view of a collimated detector 42. One such voxel 50 is identified in FIG. 1.

The processor 46 may be adapted to analyze the data obtained by the detecting apparatus in any combination of 38 and/or 40. For example, the processor 46 may be programmed with statistical information about mass or atomic number distributions that fall within "normal" profiles. A target volume or voxel 50 or a combination of volumes or voxels 50 which deviates significantly from these profiles may be identified as "suspicious." The processor 46 can also be adapted to compare data to stored profiles indicative of a high likelihood of a particular type of threat. For example, if a region of a target shows the explicit elemental profile of an explosive substance, or of high-density materials typically used as radioactive shielding, the processor 46 may signal a positive threat detection event. The system may respond to a positive threat detection event in any of a variety of ways, including rescanning the region at a higher resolution, performing a different type of scan (such as a NRF scan) for particular materials, displaying an image of the target contents, and/or signaling a human operator.

The detection methods thus described, in which scattering from the target 20 and target contents 22 is detected by detectors 42 in detector array 38 and/or 40, may be employed to obtain three-dimensional imaging of the target contents 22. For example, if the average atomic number is determined in each voxel 50 according to the methods described herein, then these data may, if desired, be reconstructed as a three-dimensional image of the target contents 22 displaying the spatial distribution of average atomic number. Similarly, using measurements of the mass in each voxel, a three-dimensional distribution of mass throughout the target may be constructed as an image.

In the embodiment illustrated in FIG. 1, the system may also include a direct transmission detector 24, such as an X-ray imager, which can measure the intensity and/or energy of photons transmitted through the target 20 as a function of the position at which the photon beam 34 strikes the target 20 (or, for a bremsstrahlung source, as a function of the position at which the electron beam strikes the bremsstrahlung target). Such a measurement could be used, for example, to obtain a map of the average density of the target 20, projected along the axis of the photon beam 34. In this way, a very precise image of the transmission density of the target can be constructed. Such an image will identify specific areas of high material density in the target which would be a further aid in detecting explosive or high atomic number materials. (Similar density imaging could also be achieved by detecting the back-scatter from the target 20, especially at low energies). A transmission detector 24 may also be employed to measure the total photon flux transmitted through the target 20, with or without spatial resolution, as a function of energy.

Figure 2:
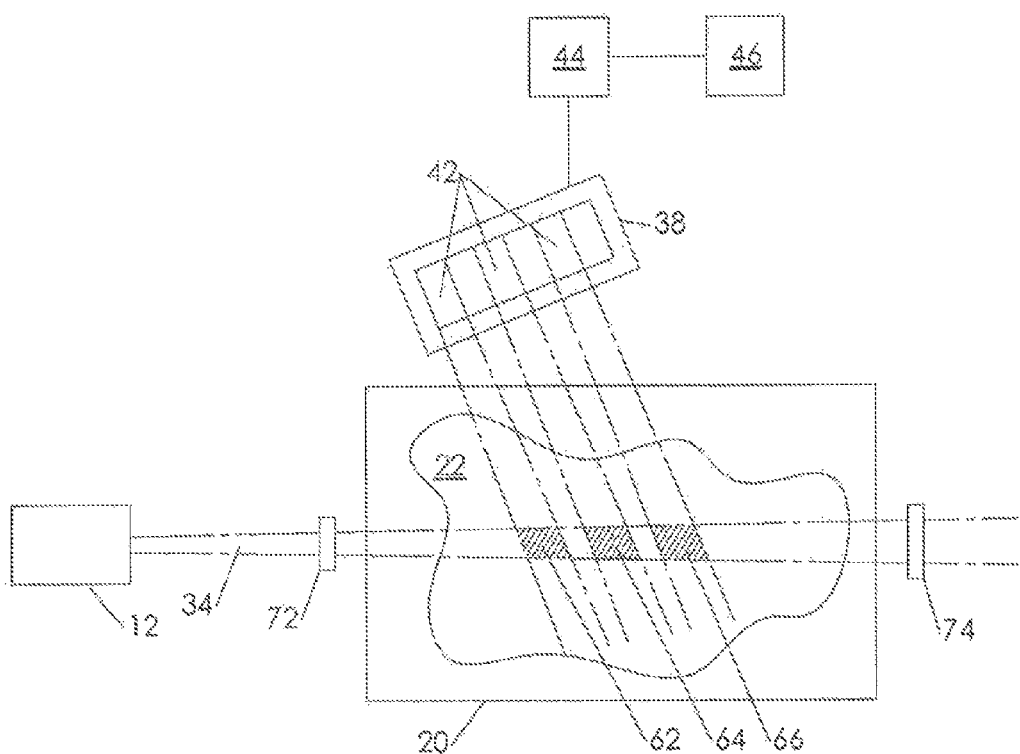
FIG. 2 is a schematic diagram of a detail of an exemplary apparatus for determining average atomic number and mass in several voxels of a target container.

An exemplary system for achieving non-intrusive inspection of a target container is further illustrated schematically in FIG. 2. A collimated beam 34 of photons impinges on the target 20. This collimated photon beam 34, as described above, may have a continuous spectrum in an energy region of interest, and can be produced by a variety of mechanisms such as bremsstrahlung, radioactive decay, or other means known in the art. The intensity and energy of the photon beam before impinging on the target (the "incident flux" $F_1$) is known, either from design and control parameters, by direct measurement, or both.

In one embodiment, the incident flux $F_1$ on the target 20 may be measured, and/or monitored by inserting a flux measurement device at position 72 in the photon beam. The flux measurement device may be, for example, an electrometer and/or an ionization gauge, where the photon beam passes through a material having known interaction cross-section with photons at the energies of the photon beam 34. The flux measurement device then measures the current created as the photon beam interacts with the material and outputs the incident flux $F_1$, preferably as a function of photon energy. (A similar flux measurement device 74 may be present downstream of the target 20 for measuring the exit flux, as discussed below).

Photons scattered from the target and/or its contents may be detected in a photon detector 42 or an array 38 of photon detectors, which may be collimated to view a particular portion of the target. The spatial volume viewed, by a photon detector in this example is determined by the cross sectional area of the beam and the detector view along the collimation axis of the detector. (As noted above, the portion of the target volume viewed by a photon detector, the intersection in space of the path of the photon beam 34 with the field of view of a detector 42, is referred to as a "voxel," which is a volume element of the three-dimensional space of the target container. The precise shape of each voxel, which may be irregular, is determined by the shape and geometry of the beam and the geometry of the collimated view of each detector.) In the embodiment illustrated schematically in FIG. 2, an array 38 of detectors 42 may simultaneously view photons scattered from multiple voxels, for example, voxels 62, 64, 66 along the beam 34. The array 38 of collimated photon detectors can be replaced by a single photon detector (or any number) that can change viewing volume without any loss of generality to the method herein described. The photon detectors 42 measure the number and energy distribution of photons scattered in the measurement direction θ measured with respect to the incident beam direction. The rate (or integral or number of photons for fixed time counting) and shape of the energy spectrum of photons scattered into each detector is dependent on (i) the intensity and energy distribution of the incident photon flux reaching the voxel viewed by the detector; (ii) the density and composition of the viewed voxel; (iii) the angle θ at which the detector is aimed, relative to the incident photon beam; (iv) the efficiency and energy resolution of the photon detectors; and (v) the density and/or composition of the material between the voxel and the detector.

Figure 3:
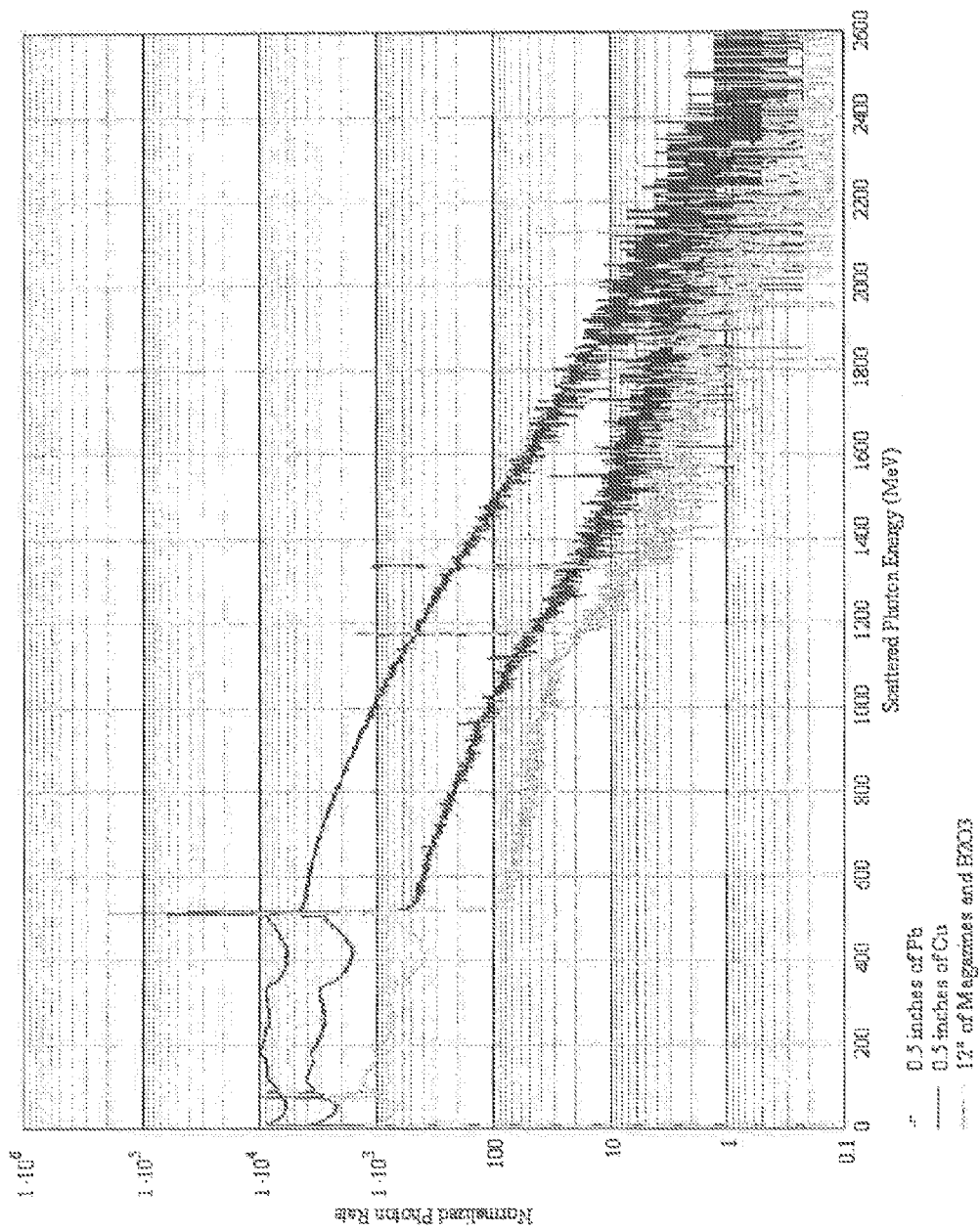
FIG. 3 is a plot of the energy distribution of scattered high-energy photons from target samples of lead, copper, and boron oxide ($B_2O_3$) surrounded by paper.

FIG. 3 illustrates the dependence of the scattered photon energy spectra upon the composition of the portion of the target being probed. In FIG. 3, the energy spectra of photons scattered at 130 degrees (relative to the direction of the photon beam 34) from targets of lead, copper, and $B_2O_3$ powder surrounded by layers of paper sheets (magazines), are shown for similar incident photon beams. An important feature in FIG. 3 is the large difference in amplitude of the photon energy spectra for energies outside the positron annihilation peak at 511 keV. As illustrated in the figure, the photon intensity outside the annihilation peak increases with increasing Z. For example, as illustrated in the figure, the photon energy spectrum for lead (Z=82) for energies greater than 511 keV shows approximately an order of magnitude greater photon intensity over that of other, lower-Z scattering materials of comparable or greater irradiated mass. The photon energy spectrum for energies below the 511 keV peak shows a similar increase in photon intensity with increased Z, and may also be used for the Z measurement technique described below. However, at energies below approximately 1.50 keV, the photon energy spectrum becomes dominated by the effects of the K edge in the target material and/or any shielding materials that may be present. These lower energies are therefore not ideal for the average Z measurement.

The features illustrated in FIG. 3 are general and may be observed in scattered photon energy spectra obtained by irradiation of a sample with, for example, a photon bremsstrahlung beam with end-point energy greater than 1 MeV. As will be understood by those skilled in the art, similar photon energy spectra would be observable for a variety of detector geometries, including without limitation any detector placed with a viewing angle of greater than approximately 90° relative to the incident photon beam.

The scattered photon energy spectra such as those illustrated in FIG. 3 have a general and important feature that forms the basis of a rapid detection scheme for identifying high-Z materials. The part of the photon energy spectrum scattered at angles greater than approximately 90 degrees relative to the bremsstrahlung beam and at energies well below the endpoint of the bremsstrahlung beam is very dependent on the Z of the material. As an example, a sample of lead presents about an order of magnitude more intensity than a similar mass of copper. The Z-dependence of features of this photon energy spectrum, can be used as described below for identifying and/or mapping the average atomic number of the contents of a target container.

In addition, as will be fully described below, the measured average Z in a voxel of the inspected target material, obtained by the method described below, together with the measured absolute scattered photon intensity can be used to determine the total mass of the voxel.

Exemplary Methods

The following methods may be used to non-intrusively inspect a target container and identify the average Z of the contents. As illustrated schematically in FIGS. 1 and 2, a photon beam 34 is made to impinge on a target 20. The photon beam may be scanned perpendicular to a face of the target container. The target container may be moved through the system perpendicular to the beam direction and to the scanning direction allowing every region of the container to be examined. As shown schematically in FIG. 2, for every position of the beam the collimated detectors interrogate a voxel where the beam and the collimated view of the detectors intersect (the voxels interrogated by the detectors may be disposed adjacently; the illustrated voxels 62, 64, and 66 of FIG. 2 have been spatially separated for clarity of illustration). The inspection system may include processor 46, programmed to dynamically analyze the data from the detector array to rapidly determine the average atomic number Z, mass of material, and/or limits on the mass of a particular material in each voxel irradiated by the beam, using the methods described below.

An exemplary inspection system may include data acquisition electronics for collecting photon counts and/or energy distribution, from the photon detectors. In addition, the processor may be further programmed with threat detection heuristics that determine whether to take further action dependent upon the result of analyzing the collected data. Such further action may include notifying a human operator of a potential threat or triggering further measurements to be initiated and/or conducted either by an automated system or by human operators. For example, the system may be programmed to alert an operator or conduct further measurements upon detection of the presence of materials having average Z in a specified range or above a threshold value. Such further measurements may include higher-resolution scans of selected regions of the target. Further measurements may also include scanning the target with other scanning methods, including NRF imaging, for further analysis of the isotonic contents of the target or a portion of the target. An exemplary system for determining the average Z and/or mass distribution in a target may use the same detectors for both the average Z and/or mass measurements, and any additional NRF imaging of the target. Alternatively, an additional set of detectors may be supplied for further imaging. As illustrated in FIG. 1, the system may include detector arrays 38 and/or 40 that may be used for NRF imaging such as described in U.S. Pat. Nos. 5,115,459, and 5,420,905. Also as illustrated in FIG. 1, the system may be configured for transmission NRF detection using reference scatterers 28 and detector array 36, also as described in U.S. Pat. Nos. 5,115,459, and 5,420,905.

In some embodiments, processor 46 may be configured to represent the average Z values and/or average density for each voxel graphically on a visual display, such as with color or shading, to form a two- or three-dimensional image of the container's contents. The processor may also be configured to display regions of the container having average atomic number above some threshold value.

Determination of the Average Atomic Number:

The average Z, $S_{av}$, of the material in a voxel is determined in the first approximation by the ratio of measured photon counts in two energy regions of the energy spectra of the scattered photons. (The terms "photon spectrum," "energy spectrum," and "photon energy spectrum" are used interchangeably throughout the present disclosure to refer to the photon energy spectral distribution, or the number of counts detected in each energy channel.) For example, region 1 may include the 511 keV line produced from positron production and annihilation in the target voxel and, region 2 may include an energy band beginning at 600 keV and extending toward some higher-energy limit programmed or entered into the data reduction system. The higher energy region can be quite broad; in an exemplary embodiment it begins at 600 keV and extends upwards to about 2 MeV. In an alternative embodiment, either or both regions may be as a narrow as a single detection channel if counting statistics are adequate. The exact energy limits will be determined by the specific requirements of a particular application, and may depend upon the counting statistics, detector resolution, or signal-to-noise ratios obtained in the higher energy channels in a particular application. It will be understood that 600 keV is an arbitrary limit, and any energy range may be used that excludes the 511 keV peak, although, as discussed above, energies above 150 keV may be preferable. In practice, the higher-energy region may be selected by choosing a center energy and then selecting a width such that the statistical fluctuations over that region are no longer dominated by noise.

Figure 4:
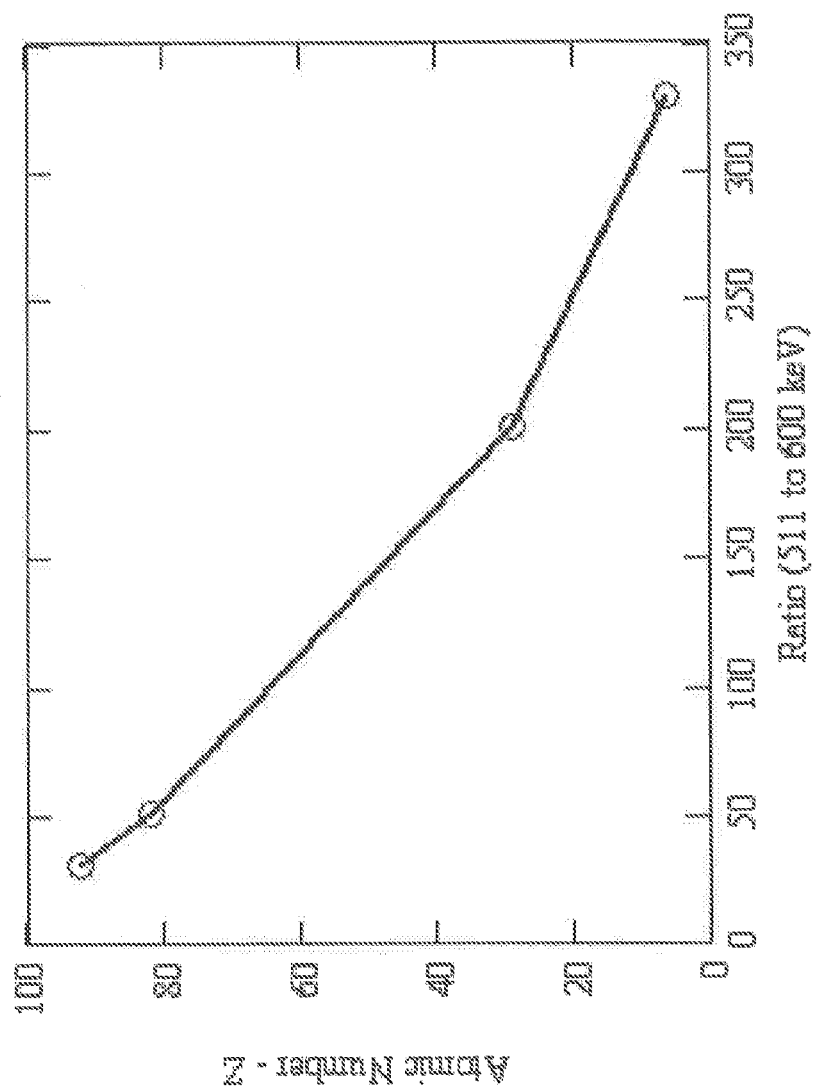
FIG. 4 illustrates the atomic number of target sample as a function of ratio of scattered photon intensities at 511 keV and at 600 keV.

Let R(Z) represent the ratio of the scattered photon intensity in region 1 to the scattered photon intensity in region 2. In FIG. 4, R(Z) is plotted for approximately equal effective masses of material with Z=92, 82, 29, and ~7 (uranium, lead, copper, and $B_2O_3$ surrounded by paper, respectively). In FIG. 4, $E_1$ was chosen so that the numerator of R(Z) was the integral under the 511 keV peak; $E_2$ was approximately 600 keV+/−5 keV.

As can be seen from FIG. 4, the dependence of R(Z) upon atomic number Z is quite pronounced. Generally, the higher the average Z in the target, the lower the value of R(Z). The ratio is largely independent of the total mass of material contained in the voxel. Thus, the average Z in a voxel may be determined by counting photons scattered in each of an appropriately selected energy region 1 and 2; completing the ratio R(Z), and comparing the result to an R(Z) curve such as that shown in FIG. 4. The known R(Z) curve used for this comparison may be determined empirically by placing test targets of known Z in the path of the beam, and measuring R from several such test targets having a range of Z. Alternatively, an R(Z) curve could be determined by analytic or statistical modeling of the interactions occurring in the target.

It should be noted that depending upon the size of the interval $E_1$ that includes the annihilation peak, a subtraction of the continuous portion of the photon energy spectrum in this energy Interval may be desirable before computing the ratio R(Z). For example, if the detector has a broad energy resolution (relative to the width of the 511 keV peak), the interval $E_1$ may include contributions from the continuous portion of the photon energy spectrum. In order to get an accurate measure of the normalized counts in the annihilation peak, these contributions may be estimated and subtracted out. In an exemplary embodiment, the contributions of the continuous portion may be estimated by averaging the continuous portion of the photon energy spectrum on either side of the energy interval $E_1$.

In some embodiments, the photon intensify in region 1 may be measured in a different scattering direction from the photon intensity in region 2. In such an embodiment, the photon intensity in one of the two regions may be corrected for the difference in measurement angle prior to computing the ratio. The correction can be determined empirically, analytically, or by statistical modeling to determine the angular distribution of scattered photons and/or any differences in detection efficiency between the detectors.

In another exemplary embodiment, the scattered photon energy spectrum from a voxel can be used in conjunction with the photons scattered from neighboring regions of the target to indicate the presence of a high-Z material, as follows. Presence of a significant quantity of high-Z material in one voxel may result in strong absorption of the beam, which in turn results in a reduced flux incident upon the voxels downstream in the beam path. Thus, the energy spectra of photons scattered from downstream voxels may exhibit a reduction in signal strength. Similarly, if a high-Z material is present in between the voxel under interrogation and the detector (out of the path of the photon beam), then the photons scattered from the voxel under interrogation may be attenuated by absorption on their way to the detector, causing a reduction in signal from the interrogated voxels. In an exemplary embodiment, a threat-detection system may look for such spatial correlations in the attenuation of the signal and use them to determine or verify the presence of a high-Z material both along the beam and/or along the path from the voxel under interrogation to the detector. For example, when such a correlation is detected, it may alert an operator and/or trigger further investigation of the target or of a region of the target, such as with NRF imaging.

Determination of the Mass:

The mass of the material contained in each voxel can be estimated by an iterative method using as input the number of photons measured in the continuous region of the photon energy spectrum above a given energy, such as 600 keV (see FIG. 3). The choice of energy region is arbitrary, and any region may be used that provides adequate counting statistics. The optimal energy regions for a particular application will depend upon the design specifics of the scattering system. The energy regions used in a particular application may be selected empirically by adjusting parameters until the greatest sensitivity for mass determination is achieved. Alternatively, energy regions may be selected using statistical modeling methods to compute estimated optimum values.

In an exemplary embodiment of this method, the mass in the first voxel interrogated by the photon beam is determined using the incident flux $F_1$, and then the mass is used to estimate the flux incident upon the next voxel in the beam path, and so on along the beam, as follows. Referring to FIG. 2, which schematically illustrates the detection of scattered photons from several voxels along the beam path, the photon count from the i'th voxel, $S_i$, into direction $\theta$ with energies falling in the range $E_\gamma$, is given by:

$$S_i(E_\gamma, \theta, Z_i) = G_i(E_\gamma, \theta, Z_i) F_i M_i \quad \text{Equation 1}$$

Using Equation 1, the R(Z) ratio is given by:

$$R_i(\theta, Z_i) = S_i(E_1, \theta, Z_i)/S_i(E_2, \theta, Z_i) = G_i(E_1, \theta Z_i)/G_i(E_2, \theta, Z_i) \quad \text{Equation 2}$$

where $G_i(E_\gamma, \theta, Z_i)$ is a known factor dependent on the average Z value ($Z_i$), the energy of the measured photons and the angle $\theta$ of scattering from the i'th voxel, $F_1$ is the total photon flux entering the i'th voxel; and $M_i$ is the mass contained in the i'th voxel. (If the voxel under consideration is the very first target voxel struck by the incident beam, then $F_1$ is the incident flux $F_1$ discussed above.) As discussed above, $E_1$ preferentially includes the annihilation peak at 511 keV, while $E_2$ is preferably some higher energy range. Also as discussed above, depending upon the size of the interval $E_1$ that includes the annihilation peak, a subtraction of the continuous portion of the photon energy spectrum in this energy interval may be desirable.

The factor $G_i(E_\gamma, \theta, Z_i)$ may be determined either empirically or by analytical or statistical modeling. $G_i(E_\gamma, \theta, Z_i)$ is referred to herein as the scattering kernel. It represents the flux or number of photons scattered in the measurement direction $\theta$, scattered from a material having atomic number $Z_i$ and mass normalized to 1 gram, for a unit total incident flux per $cm^2$. The kernel depends upon the parameters defining the shape of the flux incident upon the i'th voxel. For example, for a bremsstrahlung source, the kernel depends upon the endpoint energy of the electron beam used to generate the bremsstrahlung photons. Thus, the kernel must be determined for the particular photon source used in any given embodiment.

Data tables or analytic expression of the kernel $G_i(E_\gamma, \theta, Z_i)$ may be provided to the processor, in data reduction, software that uses Equation 1 to determine the mass $M_1$ in the i'th voxel. For example, the kernel $G_i(E_\gamma, \theta, Z_i)$ could be determined in advance empirically by placing test targets of known $Z_i$ and known $M_i$ in voxel i, and measuring $S_i$ using known incident photon flux $F_i$ for several such test targets having a range of average $Z_i$. Where such test masses are used, the calibration of the G measurement must take into account the size of the interrogated voxel. This can be achieved by, for example, using test targets of smaller cross-sectional area than the incident photon beam. Then the product of the areal density of the test target and the cross-sectional area of the test target provides the total mass of the interrogated voxels for the calibration. Alternatively, instead of direct measurement, the kernel $G_i$ could be determined by Monte Carlo modeling of the interactions occurring in the target and incorporating the detector and beam geometry. Or, the kernel $G_i$ could be determined by analytic modeling either in advance or in real time. Thus, exemplary values may be stored by the system in data tables or as analytic expressions. Regardless of how the factor $G_i$ is determined and stored, its values will be referred to herein as "predetermined values." Generally, the factor $G_i(E_\gamma, \theta, Z_i)$ incorporates the Z-dependence and spatial dependence of the scattering cross-section, the energy distribution of the photons incident on the i'th voxel (which, when a bremsstrahlung source is used, is dependent upon the spectrum of the electron beam used to create the bremsstrahlung source), as well as the detector geometry.

The average Z in each voxel $Z_1$ along the beam may be determined by, for example, the ratio method discussed above. Using the average atomic number $Z_1$ in the first voxel to evaluate $G_1$, together with the measured scattered photon count $S_1$ from the first voxel and the known initial photon flux $F_1$, the average mass $M_1$ in the first voxel may be determined from Equation 1.

The attenuation resulting from interaction of the incident photon beam with the contents of the first voxel can be estimated from the extracted values of $Z_1$ and $M_1$, so that the flux $F_2$ incident on the second voxel (the next voxel along the beam) can be estimated. Using the average atomic number $Z_2$ in the second voxel (determined, for example, using the ratio method described above) to evaluate $G_2$, together with the measured scattered, photon count $S_2$ from the first voxel and the estimated photon flux $F_2$ incident on the second voxel, the mass $M_2$ in the second voxel may be determined from Equation 1. The processor may be programmed to repeat this calculation for all voxels along the beam, estimating the flux $F_i$ incident on each voxel, and using the average Z value $Z_i$ to compute the mass $M_i$ for each voxel.

In one embodiment, the values $Z_i$, or $M_i$, or both, are represented, for example, by colors or shading or points plotted on a visual display to create an image of the mass- or Z-distribution along the beam. By scanning the beam through the target and repeating this process, a 3-D image of the target's contents may be constructed.

In another exemplary embodiment, die exit flux from the container may be measured, to provide an additional constraint on the mass determinations. The exit flux and its energy spectrum $F_E(E)$ may be measured, similarly to the measurement of the initial flux $F_1$ described above, by placing a flux measurement devise in the beam path downstream of the target, as illustrated schematically by reference number 74 in FIG. 2. Alternatively, the exit flux may be determined by other types of transmission detection in the beam path, as illustrated schematically in FIG. 1. For example, transmission detector 24 may be an X-ray imaging detector that can provide spatial information about the transmitted flux as well as a measurement of the total transmitted flux. As another example, the exit flux may be deduced from transmission NRF measurements using reference scatterers 28 and detector array 36. The exit flux measurement can provide an additional constraint to the mass measurement as follows.

The step by step derivation of the mass in each successive voxel terminates at the end of the container with a predicted exit flux, $P(E)$, where the explicit energy distribution of the flux as well as the total flux may be predicted, based upon die energy distribution of the incident flux and of the measured scattered photons. This flux may be compared to the measured exit flux $F_E(E)$ to correct the predicted mass measurement. To begin an exemplary process of correcting the predicted mass distribution, the energy averaged flux difference, $D(E)=F_E(E)-P(E)$, may be used to change the mass of each voxel along the path according to the influence on the total photon flux of the original $Z_i$ and $M_i$. That is, the difference D is apportioned to each voxel in proportion to the attenuation of that voxel to the transmitted flux in the process of the derivation of $Z_i$ and $M_i$. Next, this first order mass distribution is modified in a minimization procedure so that the incident flux energy distribution and the exit flux energy distribution match as closely as possible. In addition, the energy spectrum of the exit flux may be compared to that of the predicted exit flux $(P)E$, and the measured average Z of each target voxel may similarly be adjusted in the minimization process, in particular to take advantage of the large variation of the energy-dependence of photon absorption with Z.

In another embodiment, aspects of the voxel geometry, such as diameter or orientation, may be varied to improve the comparison between the predicted and measured exit flux energy spectrum and/or refine the measurements of mass in each voxel. For example, a redefined voxel having twice the area, but one-half the thickness, of the original voxel may contain the same mass, but yield a very different photon attenuation. (Mathematically, this is captured in the geometry dependence of $G_i$, the scattering kernel.) Such voxel redefinition may be achieved by, for example, changing the collimation of the photon beam and/or the detectors.

In an alternative embodiment, improved resolution in the average atomic number and mass estimates may be obtained by computing a correlation between R(Z) as defined above and the normalized intensity of the annihilation peak at 511 keV. This correlation may be obtained by, for example, plotting R(Z) against the integrated counts in the 511 keV peak. Because both of these variables have strong dependence upon Z, and the peak intensity depends upon the mass in the interrogated voxel, this correlation may provide improved separation between species of different atomic number and/or different masses. For example, lighter species have relatively large R(Z) (see FIG. 4) but relatively small counts in the annihilation peak, while heavier species have small R(Z) and larger numbers of counts in the annihilation peak. This correlation is illustrated in the plot in FIG. 5.

Figure 5:
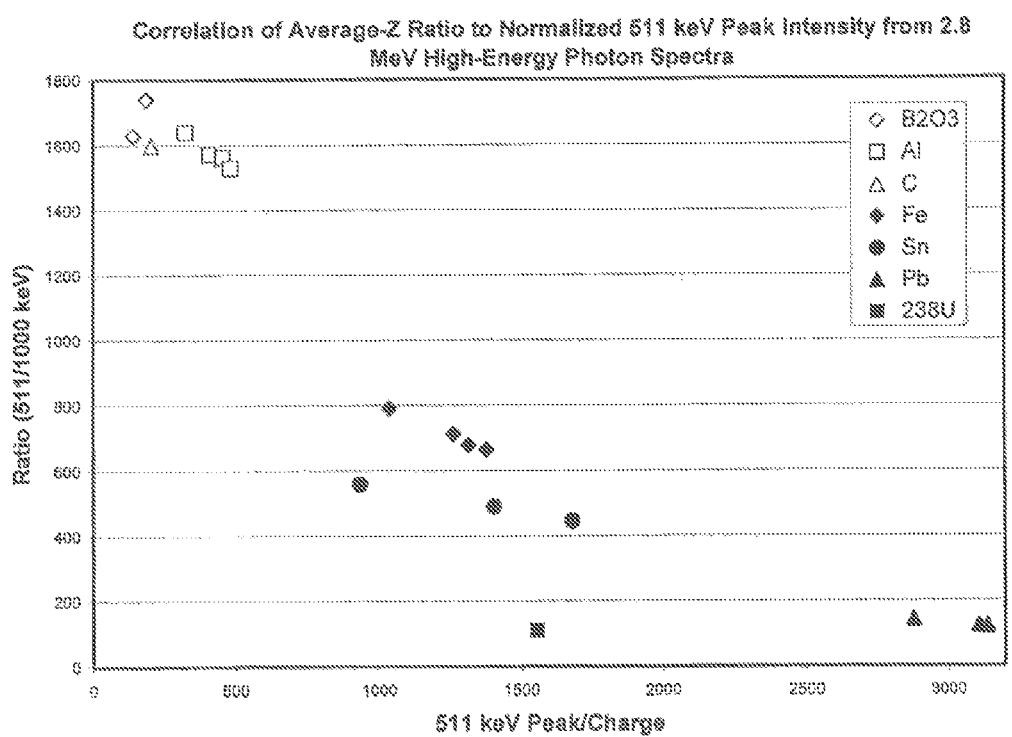
FIG. 5 is a plot of the ratio R(Z) against the number of counts in the 511 keV annihilation peak, for samples of a variety of masses and average atomic numbers.

Each point in FIG. 5 represents a different mass and of the species identified in the legend. The target masses used for the measurements in FIG. 5 are provided in Table 1 below. Each mass listed in the table corresponds to a data point in FIG. 5. The target mass can be matched with its corresponding data point by noting that the normalized annihilation peak intensity (the x-axis value) increases monotonicaliy with increasing mass for a given species. Thus, for example, the 0.54 kg Sn target corresponds to the leftmost Sn point in FIG. 5 (lowest normalized peak intensity), and the 1.61 kg Sn target corresponds to the rightmost Sn point (highest normalized peak intensity). The y-axis. R(Z), of FIG. 5 was measured and computed using the number of counts in the annihilation peak as the numerator, and the number of counts in an energy interval of +/-5 keV around 1000 keV for the denominator. The photon source was a bremsstrahlung beam generated using a 2.8 MeV electron beam.

TABLE 1

Masses of Targets Used to Generate Data in FIG. 5

| Species | Mass (kilograms) |
|---|---|
| $B_2O_3$ | 0.85, 1.24 |
| C | 1.08 |
| Al | 0.70, 1.40, 2.10, 2.8 |
| Fe | 1.07, 2.14, 3.2, 4.27 |
| Sn | 0.54, 1.08, 1.61 |
| Pb | 3.35, 6.69, 10.04 |
| U | 1.10 |

From the data in FIG. 5 it can be seen that a given measured value of R(Z) may correspond to more than one average atomic number. This is so because of experimental uncertainty in the measured value of R(Z), and may be particularly problematic for lower average atomic numbers, where background effects such as ambient scatter can dominate the R(Z) measurement. As an example, from FIG. 5 it can be seen that a measured R(Z) of approximately 1600 may be observed using samples of carbon, $B_2O_3$, or aluminum.

Plotting R(Z) against the normalized annihilation peak intensity, however, can provide improved separation, facilitating the distinctions among different species that may yield similar measured R(Z) values. This is so because for a given voxel geometry and a given average atomic number, there is a limit to how much mass can be present in a voxel. Thus, for a given value of R(Z) that could correspond to more than one average atomic number, a high peak intensity suggests the presence of denser material, increasing the probability that the voxel has a higher average atomic number. As an example, from FIG. 5 it can be seen that while certain samples of carbon, $B_2O_3$, or aluminum all yield measured ratios of approximately 1600, plotting these ratios against the normalized annihilation peak intensity provides some separation among these species.

A threat-detection system may analyze such correlations between measured R(Z) and measured annihilation peak Intensity to distinguish among multiple possible average Z values. Alternatively, the system may, given the measured R(Z) and annihilation peak intensities, compute and output probabilities that the voxel contains certain mass/average Z combinations (probability $p_A$ that the voxel contains a mass $M_A$ of material with average Z $Z_A$, and/or probability $p_B$ that the voxel contains a mass $M_B$ of material with average Z $Z_B$). For example, consider the data shown in FIG. 5 for sample of carbon and aluminum. Since certain samples of both of these species yield a measured R(Z) of approximately 1600, the R(Z) measurement alone cannot distinguish between them. However, if the normalized annihilation peak intensity is relatively high (for example, about 450), the probability may be quite low that a sufficient amount of the light element carbon may be present in the voxel under interrogation to yield the measured peak intensity. In contrast, the probability may be considerably higher that a sufficient amount of the relatively heavier element aluminum may be present. The system may, in some embodiments, employ threat-detection heuristics that use such probabilities to determine whether to notify an operator, sound an alarm, and/or trigger farther scanning such as NRF imaging or other imaging.

It should be noted that the measured annihilation peak intensity may need to be normalized for one or more factors in constructing a correlation such as that shown in FIG. 5. First, an overall normalization for incident flux may be required. In some embodiments, this overall normalization may be based upon the brightness of the incident beam. For example, in the illustration in FIG. 5, the number of counts in the annihilation peak was normalized to the total charge on the bremsstrahlung target used to generate the beam (live time×electron beam current). Alternatively, where the incident flux upon each voxel is estimated as described above, the annihilation peak intensity may be normalized to that estimated incident flux. In addition, a second, more sophisticated normalization factor may be applied where necessary or desired for refinement of the correlation. This additional normalization takes into account the effects of the geometry of the voxel, as described above in connection with determining the scattering kernel G.

Limits of the Mass of High-Z Material:

A voxel may contain a mixture of materials with the measured values of Z and M resulting from the summation of the elemental scattered photon distributions. (For the purposes of this discussion, the measured values of Z and M in a given voxel will be denoted by $Z_m$ and $M_m$ respectively.) For example, for two materials, one will have $Z_H > Z_m$, and mass $M_H$, and the other $Z_L < Z_m$, and mass $M_L$. In this case, the following relation holds for a given voxel:

$$M_m = M_H + M_L.  \quad \text{Equation 3}$$

For each energy region of the scattered photon energy spectrum, the following relationship holds:

$$G(E_\gamma, \theta, Z_m) M_m = G(E_\gamma, \theta, Z_H) M_H + G(E_\gamma, \theta, Z_L) M_L. \quad \text{Equation 4}$$

Where flux, F, incident on the voxel, divides out. Eq. 4 can be used to set a limit on the mass $M_H$ by setting $Z_L$ to the lowest value for which $G(E_\gamma, \theta, Z_L)$ has been measured. Using Equation 3 and Equation 4:

$$M_H = M_m [G(E_\gamma, \theta, Z_m) - G(E_\gamma, \theta, Z_L)] / [G(E_\gamma, \theta, Z_H) - G(E_\gamma, \theta, Z_L)] \quad \text{Equation 5}$$

As can be seen from the exemplary data in FIG. 3, in the limit of $Z_L$ small compared to $Z_m$, $G(E_\gamma, \theta, Z_L)$ is much less than $G(E_\gamma, \theta, Z_m)$. Also, $G(E_\gamma, \theta, Z_L)$ is much less than $G(E_\gamma, \theta, Z_H)$. With these approximations, Equation 5 reduces to:

$$M_H = M_m [G(E_\gamma, \theta, Z_m) / G(E_\gamma, \theta, Z_H)] \quad \text{Equation 6}$$

As an example using the data from FIG. 3, with $Z_m = 29$, $Z_H = 82$, $M_H \sim \frac{1}{10} M_m$.

The following example illustrates an alternative method of computing a limit for the mass $M_H$.

Defining $G_i(0.51\ \text{MeV}, \theta, Z_i) = G^a(Z)$ (G of the annihilation peak), and $G_i(0.6\ \text{MeV}, \theta, Z_i) = G^c(Z)$ (G of the continuum energy chosen for the measurement, where 0.6 MeV can be replaced by whatever energy is chosen), and assuming an admixture of the two mass components $M_L$ and $M_H$, the measured R value is given by:

$$R(Z_m) = [G^a(Z_H) M_H + G^a(Z_L) M_L] / [G^c(Z_H) M_H + G^c(Z_L) M_L], \quad \text{Equation 7}$$

which can be rewritten as $$R(Z_m) = [G^a(Z_H)/(G^c(Z_H)] [M_H + M_L G^a(Z_L)/G^a(Z_H)] / [M_H + M_L G^c(Z_L)/G^c(Z_H)] \quad \text{Equation 8}$$

This can be reduced to:

$$R(Z_m) = R(Z_H) [M_H + M_L G^a(Z_L)/G^a(Z_H)] / [M_H + M_L G^c(Z_L)/G_c(Z_H)] \quad \text{Equation 9}$$

Equation 9 can be used to estimate an upper limit the contribution of a high-Z material that is embedded into a lower Z matrix. As an example, suppose $Z_m = 29$ for a voxel of mass=$M_m$ (where $Z_m$ and $M_m$ may be measured using the methods described above). If the high Z material is assumed to be uranium, an upper limit of the contribution of uranium ($Z_H = 92$) is obtained by extrapolating $Z_L = 1$. In this example, the term $G^a(Z_L)/G^a(Z_H)$ is taken to be 1 as the data in FIG. 3 indicates, and $G^c(Z_L)/G^c(Z_H)$ is or order $\frac{1}{100}$), yielding $M(Z_H=92) < \frac{1}{7} M_m$. The simplicity of this results depends on the rapid variation of the continuum flux with Z and the relative constancy of the annihilation yield for roughly equal mass targets.

What is claimed is:

1. A method for analyzing material in a voxel of a target, the method comprising:
   (a) illuminating the voxel of the target with a photon beam;
   (b) measuring with at least one photon detector a first number of photons scattered from the voxel in a first predetermined energy range and in a first predetermined measurement direction;
   (c) measuring with at least one photon detector a second number of photons scattered from the voxel in a second predetermined energy range and in a second predetermined measurement direction;
   (d) determining in a processor a ratio of the first number of photons to the second number of photons;
   (e) determining in a processor an average atomic number of the material in the voxel using the ratio;
   (f) choosing at least one predetermined average atomic number range;
   (g) based upon the average atomic number determined not being within any chosen predetermined average atomic number range, taking no further action with respect to the voxel; and
   (h) based upon the average atomic number determined being within a chosen predetermined average atomic number range, taking an action with respect to the voxel chosen from the group consisting of: scanning the voxel at a higher resolution; performing a NRF scan of the voxel; scanning the voxel with another scanning method; displaying in an output device an image of at least a part of the target to an operator; and notifying the operator by means of an output device of a potential threat.

2. The method of claim 1, wherein the first predetermined measurement direction equals the second predetermined measurement direction.

3. The method of claim 1, wherein the first predetermined energy range equals the second predetermined energy range.

4. The method of claim 1, wherein the first predetermined energy range includes 511 keV.

5. The method a claim 4, wherein the second predetermined energy range excludes 511 keV.

6. A method for analyzing material in a voxel of a target, the method comprising:
(a) illuminating the voxel of the target with a photon beam;
(b) measuring with at least one photon detector first number of photons scattered from the voxel in a first predetermined energy range and in a first predetermined measurement direction;
(c) measuring with at least one photon detector a second number of photons scattered from the voxel in a second predetermined energy range and in a second predetermined measurement direction;
(d) determining in a processor a ratio of the first number of photons to the second number of photons;
(e) determining in a processor an average atomic number of the material in the voxel using the ratio;
(f) based upon the average atomic number determined not exceeding a predetermined average atomic number, taking no further action with respect to the voxel; and
(g) used upon the average atomic number determined exceeding a predetermined average atomic number, taking an action with respect to the voxel chosen from the group consisting of: scanning the voxel at a higher resolution; performing a NRF scan of the voxel; scanning the voxel with another scanning method; displaying in an output device an image of at least a part of the target to an operator; and notifying the operator by means of an output device of a potential threat.

7. The method of claim 6, wherein the first predetermined measurement direction equals the second predetermined measurement direction.

8. The method of claim 6, wherein the first predetermined energy range equals the second predetermined energy range.

9. The method of claim 6, wherein the first predetermined energy range includes 511 keV.

10. The method of claim 9, wherein the second predetermined energy range excludes 511 keV.

11. A method of scanning a target for potential threats, the method comprising:
(a) for each of a plurality of voxels in the target:
(i) illuminating the voxel with a photon beam;
(ii) measuring with at least one photon detector a first number of photons scattered from the voxel in a first predetermined energy range and in a first predetermined measurement direction;
(iii) measuring with at least one photon detector a second number of photons scattered from the voxel in a second predetermined energy range and in a second predetermined measurement direction;
(iv) determining in a processor a ratio of the first number of photons to the second number of photons;
(v) determining in a processor an average atomic number of material in the voxel using the ratio;
(b) choosing at least one predetermined average atomic number range;
(c) based upon the average atomic numbers determined not being within any chosen predetermined average atomic number range, taking no further action with respect to the target; and
(d) based upon a predetermined number of the average atomic numbers determined being within a chosen predetermined average atomic number range, taking an action with respect to the target chosen from the group consisting of: scanning at least one of the plurality of voxels at a higher resolution; performing a NRF scan of at least one of the plurality of voxels; scanning at least one of the plurality of voxels with another scanning method; displaying in an output device an image of at least a part of the target to an operator; and notifying the operator by means of an output device of a potential threat.

12. The method of claim 11, wherein the first predetermined measurement direction equals the second predetermined measurement direction.

13. The method of claim 11, wherein the first predetermined energy range equals the second predetermined energy range.

14. The method of claim 11, wherein the first predetermined energy range includes 511 keV.

15. The method of claim 14, wherein the second predetermined energy range excludes 511 keV.

16. A method of scanning a target for potential threats, the method comprising:
(a) for each of a plurality of voxels in the target:
(i) illuminating the voxel with a photon beam;
(ii) measuring with at least one photon detector a first number of photons scattered from the voxel in a first predetermined energy range and in a first predetermined measurement direction;
(iii) measuring with at least one photon detector a second number of photons scattered from the voxel in a second predetermined energy range and in a second predetermined measurement direction;
(iv) determining in a processor a ratio of the first number of photons to the second number of photons;
(v) determining in a processor an average atomic number of material in the voxel using the ratio;
(b) based upon the average atomic numbers determined not exceeding a predetermined average atomic number, taking no further action with respect to the target; and
(c) based upon a predetermined number of average atomic numbers determined exceeding a predetermined average atomic number, taking an action with respect to the target chosen from the group consisting of: scanning at least one of the plurality of voxels at a higher resolution; performing a NRF scan of at least one of the plurality of voxels; scanning at least one of the plurality of voxels with another scanning method; displaying in an output device an image of at least a part of the target to an operator; and notifying the operator by means of an output device of a potential threat.

17. The method of claim 16, wherein the first predetermined measurement direction equals the second predetermined measurement direction.

18. The method of claim 16, wherein the first predetermined energy range equals the second predetermined energy range.

19. The method of claim 16, wherein the first predetermined energy range includes 511 keV.

20. The method of claim 19, wherein the second predetermined energy range excludes 511 keV.

21. A system for analyzing material in a voxel of a target, the method comprising:
(a) a device for illuminating the voxel of the target with a photon beam;
(b) at least one photon detector configured to measure a first number of photons scattered from the voxel in a first predetermined energy range and in a first predetermined measurement direction;
(c) at least one photon detector configured to measure a second number of photons scattered from the voxel in a second predetermined energy range and in a second predetermined measurement direction;
(d) a processor configured:

(i) to determine a ratio of the first number of photons to the second number of photons;

(ii) to determine an average atomic number of the material in the voxel using the ratio;

(iii) based upon the average atomic number determined not being within a chosen predetermined average atomic number range, to determine to take no further action with respect to the voxel; and (iv) based upon the average atomic number determined being within the chosen predetermined average atomic number range, to determine to take an action with respect to the voxel chosen from the group consisting of: scanning the voxel at a higher resolution; performing a NRF scan of the voxel; scanning the voxel with another scanning method; instructing an output device to display an image of at least a part of the target to an operator; and instructing the output device to notify the operator of a potential threat; and (e) an output device configured to:

(i) display an image of at least a part of the target to an operator; and (ii) notify the operator of a potential threat.

22. The system of claim 21, wherein the first predetermined measurement direction equals the second predetermined measurement direction.

23. The system of claim 21, wherein the first predetermined energy range equals the second predetermined energy range.

24. The system of claim 21, wherein the first predetermined energy range includes 511 keV.

25. The system of claim 24, wherein the second predetermined energy range excludes 511 keV.

26. A system for analyzing material in a voxel of a target, the method comprising:

(a) a device for illuminating the voxel of the target with a photon beam;

(b) at least one photon detector configured to measure a first number of photons scattered from the voxel in a first predetermined energy range and in a first predetermined measurement direction;

(c) at least one photon detector configured to measure a second number of photons scattered from the voxel in a second predetermined energy range and in a second predetermined measurement direction;

(d) a processor configured:

(i) to determine a ratio of the first number of photons to the second number of photons;

(ii) to determine an average atomic number of the material in the voxel using the ratio;

(iii) based upon the average atomic number determined not exceeding a predetermined average atomic number, to determine to take no further action with respect to the voxel; and (iv) based upon the average atomic number determined exceeding a predetermined average atomic number, to determine to take an action with respect to the voxel chosen from the group consisting of: scanning the voxel a higher resolution; performing a NRF scan of the voxel; scanning the voxel with another scanning method; instructing an output device to display an image of at least a part of the target to an operator; and instructing the output device to notify the operator of a potential threat; and (e) an output device configured to:

(i) display an image of at least a part of the target to an operator; and (ii) notify the operator of a potential threat.

27. The system of claim 26, wherein the first predetermined measurement direction equals the second predetermined measurement direction.

28. The system of claim 26, wherein the first predetermined energy range equals the second predetermined energy range.

29. The system of claim 26, wherein the first predetermined energy range includes 511 keV.

30. The system of claim 29, wherein the second predetermined energy range excludes 511 keV.

31. A system for scanning a target for potential threats, the method comprising:

(a) a device for illuminating a plurality of voxels in the target with a photon beam;

(b) at least one photon detector configured to measure a first number of photons scattered from each of the plurality of voxels in a first predetermined energy range and in a first predetermined measurement direction;

(c) at least one photon detector configured to measure a second number of photons scattered from each of the plurality of voxels in a second predetermined energy range and in a second predetermined measurement direction;

(d) a processor configured:

(i) to determine for each of the plurality of voxels a ratio of the first number of photons to the second number of photons;

(ii) to determine an average atomic number of the material in each of the plurality of voxels using the ratio;

(iii) based upon the average atomic numbers determined not being within a predetermined average atomic number range, to determine to take no further action with respect to the target; and (iv) based upon a predetermined number of the average atomic numbers determined being within the predetermined average atomic number range, to determine to take an action with respect to the target chosen from the group consisting of: scanning at least one of the plurality of voxels at a higher resolution; performing a NRF scan of at least one of the plurality of voxels; scanning at least one of the plurality of voxels with another scanning method; instructing an output device to display an image of at least a part of the target to an operator; and instructing the output device to notify the operator of a potential threat; and (e) an output device configured to:

(i) display an image of at least a part of the target to an operator; and (ii) notify the operator of a potential threat.

32. The system of claim 31, wherein the first predetermined measurement direction equals the second predetermined measurement direction.

33. The system of claim 31, wherein the first predetermined energy range equals the second predetermined energy range.

34. The system of claim 31, wherein the first predetermined energy range includes 511 keV.

35. The system of claim 34, wherein the second predetermined energy range excludes 511 keV.

36. A system of scanning a target for potential threats, the method comprising:

(a) a device for illuminating a plurality of voxels in the target with a photon beam;

(b) at least one photon detector configured to measure a first number of photons scattered from each of the plurality of voxels in a first predetermined energy range and in a first predetermined measurement direction;

(c) at least one photon detector configured to measure a second number of photons scattered from each of the plurality of voxels in a second predetermined energy range and in a second predetermined measurement direction;

(d) a processor configured:
  (i) to determine for each of the plurality of voxels a ratio of the first number of photons to the second number of photons;
  (ii) to determine an average atomic number of the material in each of the plurality of voxels using the ratio;
  (iii) based upon the average atomic numbers determined not exceeding a predetermined average atomic number, to determine to take no further action with respect to the target; and
  (iv) based upon a predetermined number of the average atomic numbers determined exceeding a predetermined average atomic number, to determine to take an action with respect to the target chosen from the group consisting of: scanning at least one of the plurality of voxels at a higher resolution; performing a NRF scan of at least one of the plurality of voxels; scanning at least one of the plurality of voxels with another scanning method; instructing an output device to display an image of at least a part of the target to an operator; and instructing the output device to notify the operator of a potential threat; and (e) an output device configured to:
  (i) display an image of at least a part of the target to an operator; and
  (ii) notify the operator of a potential threat.

37. The system of claim 36, wherein the first predetermined measurement direction equals the second predetermined measurement direction.

38. The system of claim 36, wherein the first predetermined energy range equals the second predetermined energy range.

39. The system of claim 36, wherein the first predetermined energy range includes 511 keV.

40. The system of claim 39, wherein the second predetermined energy range excludes 511 keV.

* * * * *